US009087456B2

(12) United States Patent
Allen et al.

(10) Patent No.: US 9,087,456 B2
(45) Date of Patent: Jul. 21, 2015

(54) FETAL SONOGRAPHY MODEL APPARATUSES AND METHODS

(71) Applicant: SETON HEALTHCARE FAMILY, Austin, TX (US)

(72) Inventors: Buffy Allen, Austin, TX (US); Richard Drake, Austin, TX (US); Judy Kitchens, Austin, TX (US); Celeste Sheppard, Austin, TX (US)

(73) Assignee: SETON HEALTHCARE FAMILY, Austin, TX (US)

( * ) Notice: Subject to any disclaimer, the term of this patent is extended or adjusted under 35 U.S.C. 154(b) by 0 days.

(21) Appl. No.: 13/829,450

(22) Filed: Mar. 14, 2013

(65) Prior Publication Data

US 2013/0337425 A1 Dec. 19, 2013

Related U.S. Application Data

(60) Provisional application No. 61/645,317, filed on May 10, 2012.

(51) Int. Cl.
*G09B 23/28* (2006.01)
*A61B 8/08* (2006.01)
(52) U.S. Cl.
CPC ............ *G09B 23/281* (2013.01); *A61B 8/0816* (2013.01); *G09B 23/286* (2013.01)
(58) Field of Classification Search
CPC ... G09B 23/281; G09B 23/285; G09B 23/286
USPC .......................... 434/262, 267, 268, 272, 273
See application file for complete search history.

(56) References Cited

U.S. PATENT DOCUMENTS

| 2,551,560 | A | * | 5/1951 | Graves | 434/273 |
|---|---|---|---|---|---|
| 3,797,130 | A | | 3/1974 | Knapp et al. | 35/17 |
| 3,822,486 | A | * | 7/1974 | Knapp et al. | 434/273 |
| 4,531,919 | A | * | 7/1985 | Ware | 434/262 |
| 5,061,187 | A | * | 10/1991 | Jerath | 434/262 |
| 5,104,328 | A | * | 4/1992 | Lounsbury | 434/273 |
| 5,839,904 | A | * | 11/1998 | Bloom | 434/268 |
| 7,306,465 | B2 | * | 12/2007 | White | 434/268 |
| 7,465,168 | B2 | | 12/2008 | Allen et al. | 434/273 |
| 7,651,332 | B2 | * | 1/2010 | Dupuis et al. | 434/262 |
| 8,016,598 | B2 | * | 9/2011 | Eggert et al. | 434/268 |
| 8,128,413 | B2 | * | 3/2012 | Lynch | 434/273 |
| 8,323,032 | B2 | * | 12/2012 | Deering | 434/273 |
| 8,500,452 | B2 | * | 8/2013 | Trotta et al. | 434/268 |
| 8,544,113 | B1 | * | 10/2013 | Boettcher et al. | 2/69 |
| 2009/0035741 | A1 | * | 2/2009 | Riener et al. | 434/273 |
| 2010/0179428 | A1 | * | 7/2010 | Pedersen et al. | 600/443 |
| 2013/0004926 | A1 | * | 1/2013 | Klemp | 434/273 |
| 2013/0065211 | A1 | * | 3/2013 | Amso et al. | 434/262 |
| 2014/0011173 | A1 | * | 1/2014 | Tepper et al. | 434/273 |

* cited by examiner

*Primary Examiner* — Kurt Fernstrom
(74) *Attorney, Agent, or Firm* — Norton Rose Fulbright US LLP

(57) ABSTRACT

This disclosure includes embodiments of apparatuses and methods for simulating the uterus of a human (e.g., for training medical providers to perform sonograms, amniocentesis, ultrasound-guided amniocentesis, and/or other procedures). For example, in at least some embodiments, the apparatus comprises a container with a compartment and an anterior wall that is configured to permit sonogram imaging of the compartment. In some embodiments, the apparatus comprises a container that is configured to be removably coupled to the abdomen of a live human or human model such that the compartment simulates the uterus of the human or model.

23 Claims, 4 Drawing Sheets

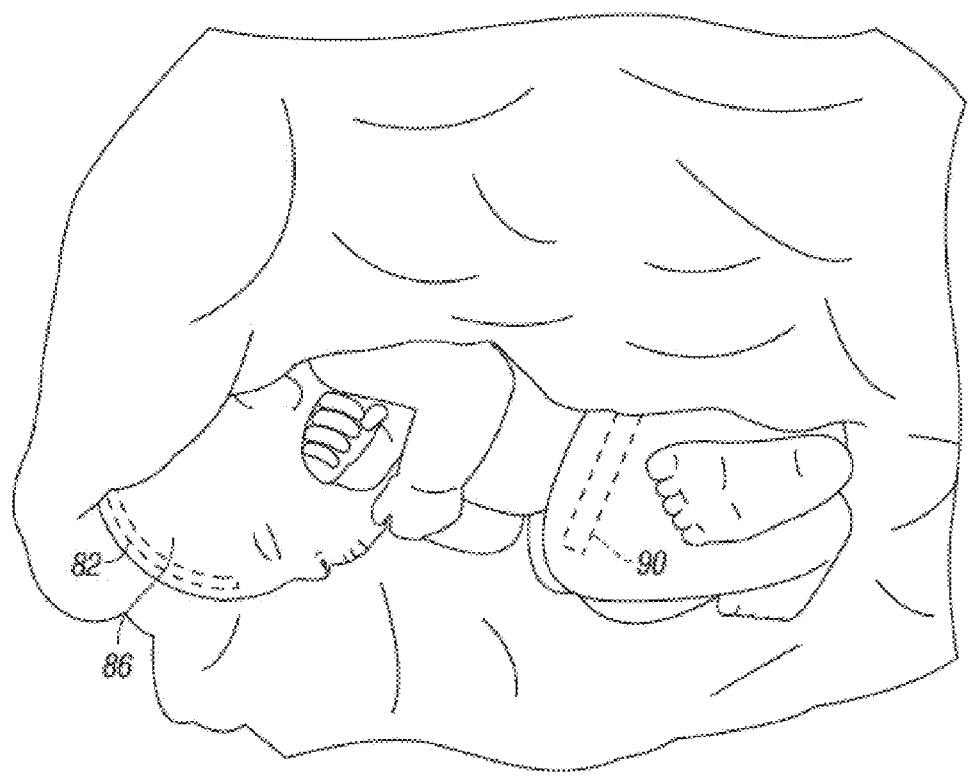
FIG. 4
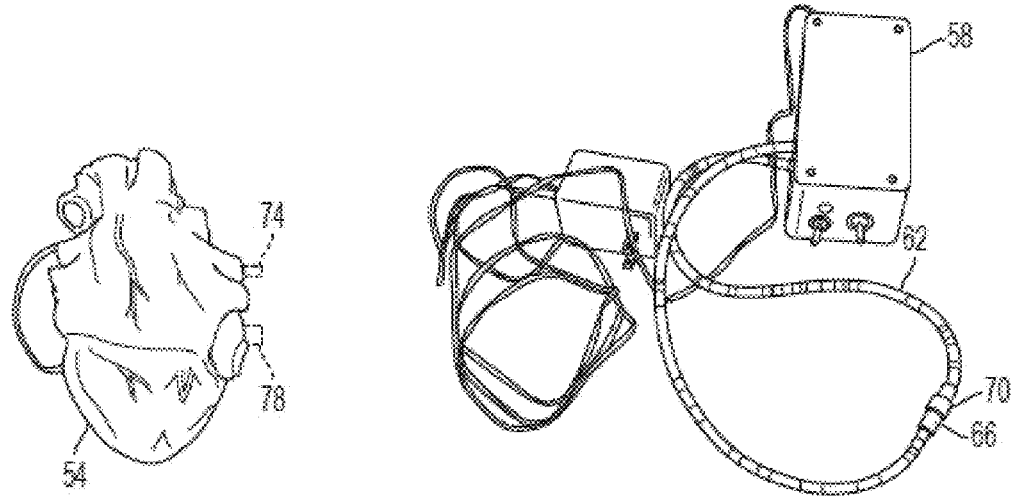
FIG. 5A  FIG. 5B

FETAL SONOGRAPHY MODEL APPARATUSES AND METHODS

CROSS-REFERENCE TO RELATED APPLICATION

This application claims priority to U.S. Provisional Patent Application No. 61/645,317, filed May 10, 2012, which is incorporated by reference in its entirety.

BACKGROUND

1. Field of the Invention

The present invention relates generally to biological simulation and, more particularly, but not by way of limitation, to apparatuses and methods for simulating a human uterus such as, for example, with a human fetus model (e.g., for training of medical providers).

2. Description of Related Art

Examples of uterine and/or fetal modeling apparatuses and methods include the Fetal Ultrasound and Biometrics Phantom available from Computerized Imaging Reference Systems (CIRS), Norfolk, Va.; the Amniocentesis Ultrasound Training Model available from Blue Phantom, Redmond, Wash.; the SonoMom system available from SimuLab Corporation, Seattle, Wash.; the Ultrasound Simulator available from Schallware GmbH, Berlin, Germany; the ScanTrainer available from MedaPhor Ltd., Cardiff, Wales, United Kingdom; and perhaps certain ultrasound phantoms available from Kyoto Kagaku Co., Ltd., Tokyo, Japan.

SUMMARY

Embodiments of the present apparatuses or models can be used as add-on or modular addition to live humans or human models to enable training of healthcare providers to perform sonograms, amniocentesis, ultrasound-guided amniocentesis, and/or other procedures. For example, the present apparatus can be disposed on the abdomen of live human such that a medical provider can interact with a live "patient" during simulated procedures for training, allowing training to include focus on communication and teamwork skills and/or managing human factors (e.g., to reduce human errors). For example, this type of human interaction during training can be especially useful for cognitive skills training in complex situations with potentially critical factors that can require numerous evaluations of current conditions, and various inputs from an interprofessional team before reaching a medical decision. The present apparatuses or models can provide unique training opportunities for healthcare professionals to face a real person with real pressure, which often is not achievable with typical stand-alone torsos, rotatable cylinder phantoms, or computer-generated images that may be used in other sonogram-training devices and methods. Embodiments of the present apparatuses can also include details (e.g., that are generally omitted from other training aids) such as, for example, a full skull, a beating heart (e.g., to enable simulation and training for fetal heart assessment, which is often a trigger point for obstetrical emergencies). Embodiments of the present apparatuses can also fit on any "standardized patient" (e.g., the abdomen of a live human or human model) with minimal adjustment. A live "patient" can feel actual weight, pressure, and fetal movement, which can be used for other obstetrical intervention practice such as leopold maneuver. The portability and flexibility of embodiments of the present apparatuses make it a convenient training device or phantom for obstetrical simulation training in a variety of circumstances, such as for, identification of fetal number and position, amniotic fluid volume assessment, fetal heart activity assessment, basic fetal anatomy landmarks for biometry, amniocentesis practice, and/or intra-uterine surgery practice.

Some embodiments of the present apparatuses comprise: a container having an anterior wall, a posterior wall, and an internal compartment; a human fetus model disposed in the compartment; and a fluid disposed in the compartment; where the anterior wall is configured to permit sonogram imaging of the human fetus model through the anterior wall; and where the container is configured to be removably coupled to the abdomen of a live human or human model such that the compartment simulates the uterus of the human or model. Some embodiments further comprise: a placenta model disposed in the compartment. Some embodiments further comprise: an umbilical cord model coupled to and extending between the human fetus model and the placenta model. Some embodiments comprise multiple human fetus models, or a single model of multiple human fetuses.

Some embodiments of the present apparatuses comprise: a container having an anterior wall, a posterior wall, and an internal compartment configured to receive a human fetus model and a fluid; where the anterior wall is configured to permit sonogram imaging of the compartment through the anterior wall; and where the container is configured to be removably coupled to the abdomen of a live human or human model such that the compartment simulates the uterus of the human or model. Some embodiments further comprise: a human fetus model configured to be disposed in the compartment of the container such that the human fetus model can be imaged through the anterior wall by sonogram. Some embodiments further comprise: a fluid configured to be disposed in the compartment of the container with the human fetus model such that the fetus can be imaged through the anterior wall by sonogram. Some embodiments further comprise: a placenta model configured to be disposed in the compartment of the container such that the placenta model can be imaged through the anterior wall by sonogram. Some embodiments further comprise: an umbilical cord model coupled to and extending between the human fetus model and the placenta model.

In some embodiments of the present apparatuses, the container comprises an access point through which fluid can be removed from or introduced into the compartment. In some embodiments, the access point is configured such that a human fetus model can be removed from or introduced into the compartment.

In some embodiments of the present apparatuses, the human fetus model comprises a hydraulic heart model, and the apparatus further comprises: a pump configured to be coupled to the heart model to simulate a heartbeat by pumping fluid to the heart model. In some embodiments, the human fetus model comprises: a skull model; and a brain model disposed in the skull, the brain model configured to be distinguishable from the skull model in a sonogram image. In some embodiments, the human fetus model comprises: one or more bone models disposed in the human fetus model, the one or more bone models configured to be distinguishable from other parts of the human fetus model in a sonogram image.

In embodiments of the present apparatuses, the anterior wall has a flexible outer surface. In some embodiments, the anterior wall comprises silicone. In some embodiments, the posterior wall comprises silicone. In some embodiments, the anterior wall is configured to be punctured by a needle, and to substantially self-seal the puncture after removal of the needle. In some embodiments, the posterior wall is configured to resist being punctured by a needle. In some embodiments, the anterior wall is unitary with the posterior wall.

Some embodiments of the present kits comprise: an embodiment of the present apparatuses and; a second human fetus model. In some embodiments, the second human fetus model is configured to represent a different stage of fetal development than the first human fetus model. Some embodiments of the present kits comprise a first one of the present apparatuses having a first human fetus model at a first stage of development; and a second one of the present apparatuses having a second human fetus model at a second stage of development that is different than the first stage of development.

Some embodiments of the present methods comprise: disposing an embodiment of the present apparatuses on the abdomen of a live human or human model such that the compartment simulates the uterus of the human or model.

Some embodiments of the present methods comprise: generating one or more images of the compartment of an embodiment of the present apparatuses using a sonogram machine. Some embodiments further comprise: disposing the apparatus on the abdomen of a live human or human model such that the compartment simulates the uterus of the human or model (e.g., prior to generating the one or more images.

Any embodiment of any of the present apparatuses and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 4 depicts an enlarged perspective view of the human fetus model of FIG. 1.

FIG. 5A depicts a perspective view of one embodiment of a hydraulic heart model for use with the human fetus model of the apparatus of FIG. 1.

FIG. 5B depicts a perspective view of one embodiment of a pump configured to pump fluid to the hydraulic heart model of FIG. 4A to simulate a heartbeat.

DESCRIPTION OF ILLUSTRATIVE EMBODIMENTS

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any embodiment of the present apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device or system that is configured in a certain way is configured in at least that way, but it can also be configured in other ways than those specifically described.

Figure 1:
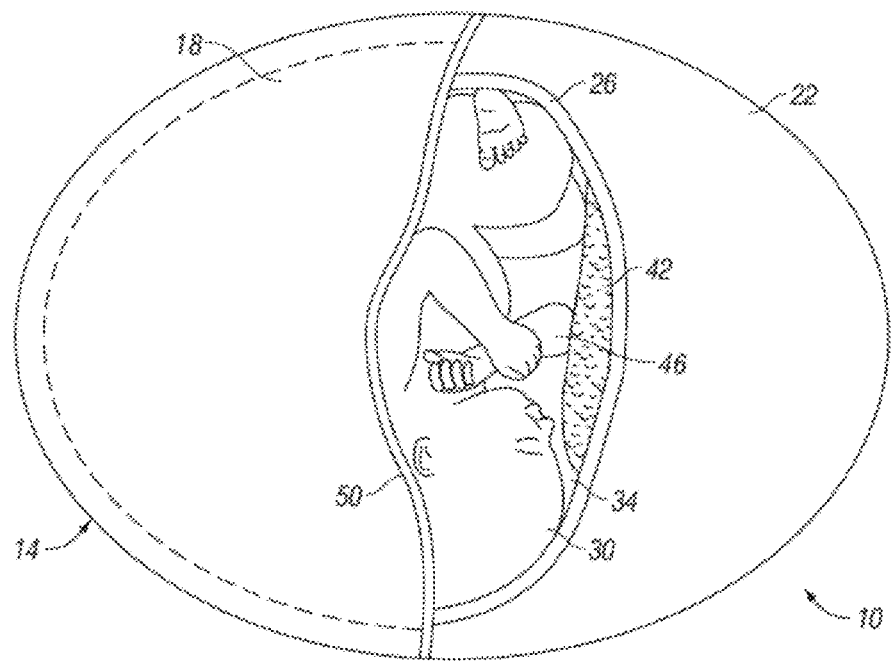
FIG. 1 depicts a cutaway view of one embodiment of the present apparatuses having a human fetus model disposed in the compartment of a container that is configured to simulate a human uterus.
Figure 2:
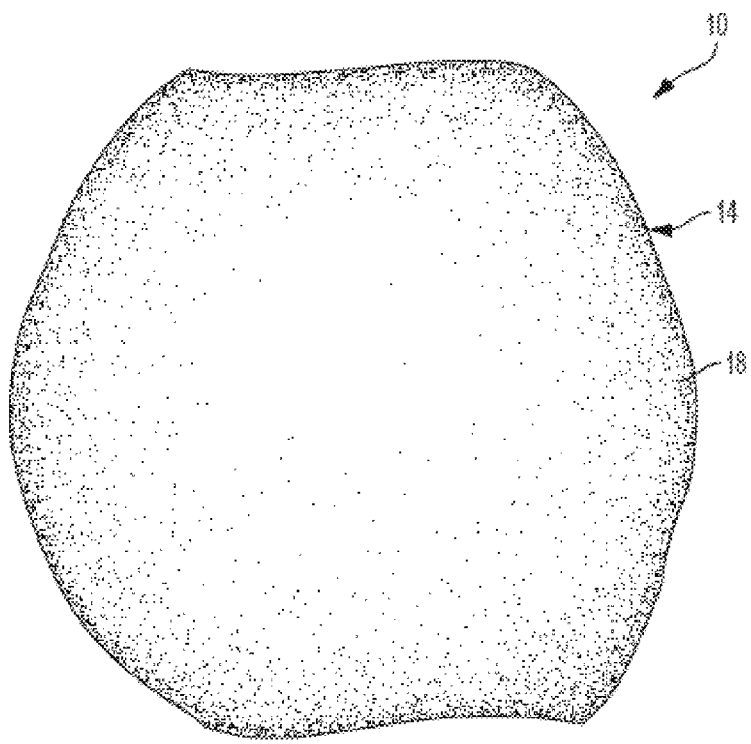
FIG. 2 depicts an upper perspective view of the apparatus of FIG. 1.
Figure 3:
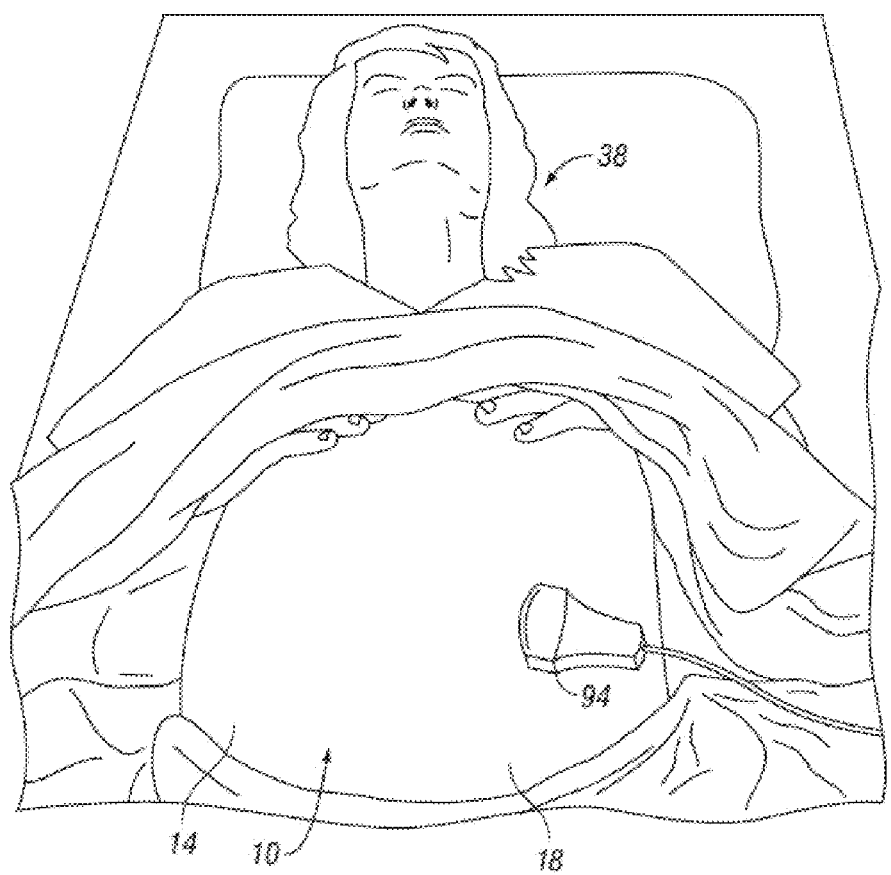
FIG. 3 depicts an upper perspective view of the apparatus of FIG. 1, shown disposed on the abdomen of a live human.

Referring now to the drawings, and more particularly to FIGS. 1-5B, shown therein and designed by the reference numeral 10 is one embodiment of the present apparatuses for simulating a human uterus. In the embodiment shown, apparatus 10 comprises a container 14 having an anterior wall 18, a posterior wall 22, and an internal compartment 26 configured to receive a human fetus model 30 and a fluid 34. In the embodiment shown, anterior wall 18 is configured to permit sonogram imaging of compartment 26 (e.g., of items disposed in the compartment) through anterior wall 18. For example, anterior wall can comprise a material that is permeable to ultrasound waves in a manner that is similar to the permeability to ultrasound waves of human tissue (e.g., between a human's abdominal skin and the interior of the uterus), and/or anterior wall 18 can of, for example, between 1 and 2 inches (e.g., greater than, or between any two of: 1, 1.2, 1.4, 1.6, 1.8, or 2 inches). In the embodiment shown, container 14 is configured to be removably coupled to the abdomen of a live human or human model (e.g., a manikin or other model of a human body or part of a human body) such that compartment 26 simulates a uterus of the human or model. For example, FIG. 3 depicts apparatus 10 coupled to (e.g., disposed on) the abdomen of a live human 38. In some embodiments, container 14 comprises one or more straps configured to extend around the abdomen of the a human or human model.

In some embodiments, anterior wall 18 can comprise a flexible outer surface 50 (e.g., the entire thickness of wall 18 can be flexible). For example, in the embodiment shown, anterior wall 18 comprises silicone (e.g., medical grade silicone), such as may be, for example, available from Smooth-On, Inc., Easton, Pa., USA. In some embodiments, posterior wall 22 also comprises silicone and/or is unitary with anterior wall 18. In some embodiments, posterior wall 22 can, for example, have a Shore A hardness of 10-20 (e.g., greater than, or between any two of: 10, 12, 14, 16, 18, or 20); and/or anterior wall 18 can have a Shore A hardness of, for example, 45-55 (e.g., greater than, or between any two of: 45, 47, 49, 51, 53, or 55). In some embodiments, anterior wall 18 is configured to be punctured by a needle, such as, for example, during simulated medical procedures (e.g., amniocentesis, ultrasound-guided amniocentesis, and/or the like), and/or to substantially self-seal the puncture after removal of the needle. For example, flexible, medical-grade silicones can provide such self-sealing properties. In such embodiments, posterior wall 22 can be configured to resist being punctured by a needle (e.g., to prevent injury to a live human on which apparatus 10 is disposed during simulated medical procedures). For example, posterior wall 22 can include a layer or liner that comprises a metallic sheet (e.g., solid or woven), a puncture-resistant fabric, and/or the like.

In some embodiments, container 14 can comprise an access point (not shown) through which fluid 34 and/or model 30 can be removed from or introduced into compartment 26. Examples of suitable access points can include one or more openings with a threaded lid, a plastic zip-lock opening, and/or any other suitable opening (e.g., between anterior wall 18 and posterior wall 22) and/or closure.

In the embodiment shown, apparatus 10 comprises human fetus model 30 disposed in compartment 26 such that model 30 can be imaged through anterior wall 18 by a sonogram (e.g., various commercially-available sonogram machines). In some embodiments, apparatus 10 further comprises: a placenta model 42 configured to be disposed (e.g., disposed, as shown) in compartment 26; and/or an umbilical cord model 46 configured to be disposed (e.g., disposed, as shown) in compartment 26 (e.g., coupled to and extending between fetus model 30 and placenta model 42). In some embodiments, apparatus 10 further comprises fluid 34 configured to be disposed in compartment 26, to simulate amniotic fluid. Fluid 34 can comprise, for example, liquid glycerin and/or saline solution. Some embodiments comprise multiple human fetus models, or a single model of multiple human fetuses.

In some embodiments, human fetus model 30 comprises a heart model 54 (FIG. 5A). For example, in the embodiment shown, heart model 54 is a hydraulic heart model configured to receive fluid from pump to simulate a heartbeat. For example, in the embodiment shown, apparatus 10 further comprises a pump unit 58 that is configured to be coupled to heart model 54 to simulate a heartbeat by pumping fluid to the heart model. For example, in the embodiment shown, pump 58 comprises a fluid tube 62 that includes a male connector 66 and a female connector 70 (shown coupled to the male connector to prevent leakage of fluid in the tube 62). In this embodiment, heart model 54 comprises a male connector 74 configured to be coupled to female connector 70 of pump 58, and a female connector 78 configured to be coupled to male connector 66 of pump 58, such that fluid can be circulated through the heart model by pump 58 to simulate a heartbeat. In the embodiment shown, pump 58 comprises an a standard plug for connection to a common alternating-current (AC) outlet. In other embodiments, pump unit 58 can comprise one or more batteries.

In some embodiments, human fetus model 30 can comprise a skull model 82 disposed in the head of model 30, and/or a brain model 86 (e.g., with two defined brain hemispheres) disposed in the skull model. Examples of skull model 82 that are suitable for at least some embodiments of the present models 30 are available from 3BScientific (www.3bscientific.com). In some embodiments, brain model 86 is configured to be distinguishable from skull model 82 in a sonogram image (e.g., brain model 86 can have a different density, Shore A hardness, and/or other properties that result in differences in appearance of the brain model and the skull model in an ultrasound image). For example, in the embodiment shown, brain model 86 can have a Shore A hardness of between 25 and 35 (e.g., greater than, or between any two of: 25, 27, 29, 31, 33, or 35). In some embodiments, skull model is unitary with the remainder of the exterior of model 30 and/or has a Shore A hardness of between 45 and 55 (e.g., greater than, or between any two of: 45, 47, 49, 51, 53, or 55). In some embodiments, human fetus model 30 comprises one or more additional bone models 90 disposed in model 30 and/or configured to be distinguishable from other parts of the human fetus model in a sonogram image (e.g., bone models 90 can have a different density, Shore A hardness, and/or other properties that result in differences in appearance of the brain model and the skull model in an ultrasound image). For example, in the embodiment shown, model 30 comprises femur bone models 90 that can comprise, for example, a metal such as steel or iron. In some embodiments, the brain model and/or heart model (and/or other organ models) can comprise silicone and/or can be dyed or otherwise colored to more-closely resemble the organs they are intended to model.

Some embodiments of the present kits comprise a container 14 and a plurality of human fetus models 30, such as, for example, a first human fetus model at a first stage of development (e.g., 25 weeks or earlier) and a second human fetus model at a second stage of development (e.g., 32 weeks, 35 weeks, or later). In some embodiments, a compartment 26 is separately defined for each of the plurality of models 30 (e.g., each of the plurality of models is disposed in a separate (e.g., silicone or plastic) bag, such that models can be interchanged into and out of container 14 without simultaneously extracting fluid from the respective compartments. Other embodiments of the present kits comprise a plurality of containers 14 each containing a different human fetus model 30, such as, for example, a first container 14 with a first human fetus model at a first stage of development (e.g., 25 weeks or earlier) and a container 14 with a second human fetus model at a second stage of development (e.g., 32 weeks, 35 weeks, or later).

Some embodiments of the present methods comprise: generating one or more images of the compartment (e.g., 26) of an embodiment of the present apparatuses (e.g., 10) using a sonogram machine (e.g., ultrasound transducer 94). Some embodiments of the present methods also or alternatively comprise disposing an embodiment of the present apparatuses (e.g., 10) on the abdomen of a live human 38 (as shown in FIG. 3) or human model such that the compartment (e.g., 26) simulates the uterus of the human or model. Some embodiments of the present methods also or alternatively comprise puncturing the anterior wall (e.g., 18) of an embodiment of the present apparatuses (e.g., 10) with a needle (e.g., an amniocentesis needle) while the apparatus is disposed on the abdomen or a live human (e.g., 98) or human model (e.g., such that the needle extends toward the live human or human model, and/or contacts the posterior wall (e.g., 22)).

Figure 6:
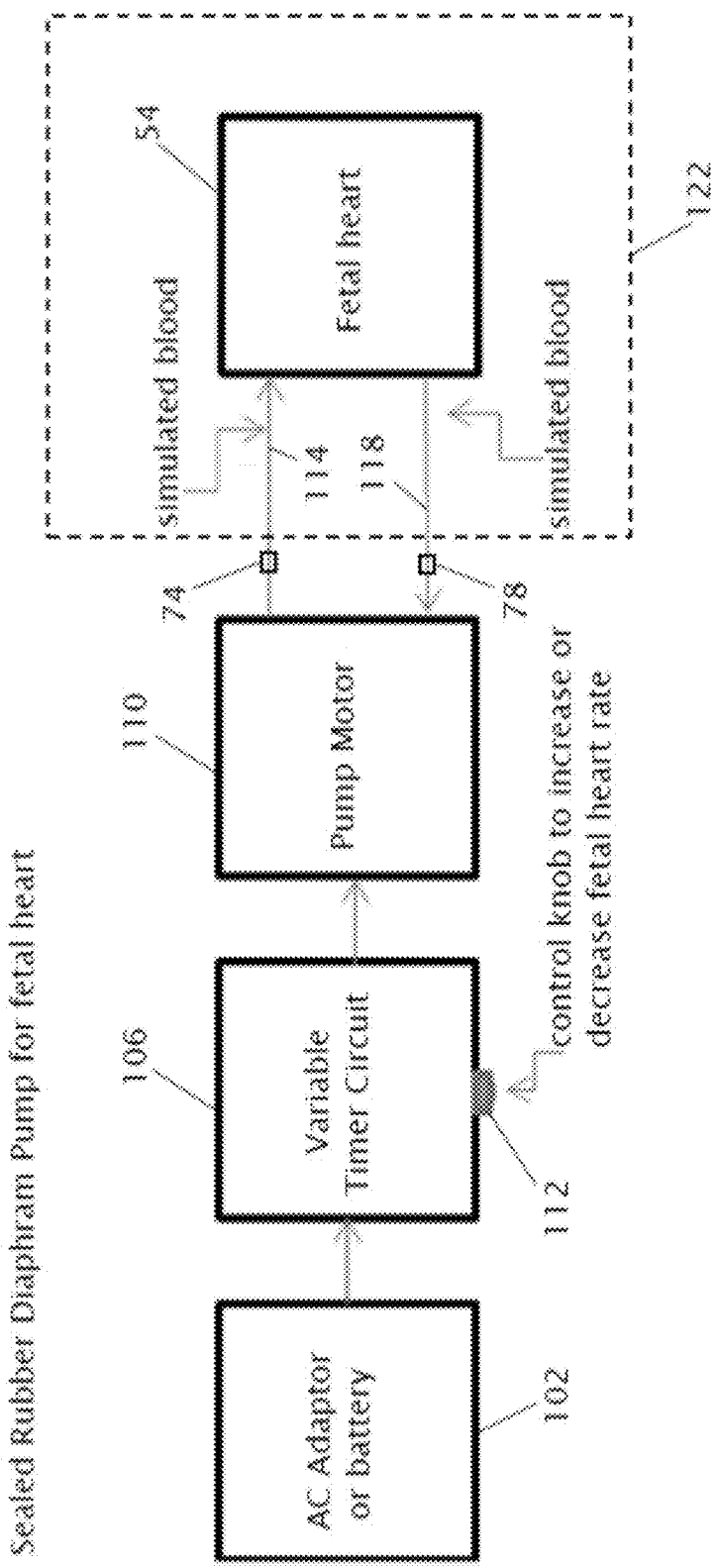
FIG. 6 depicts a block diagram of an embodiment of a pump and hydraulic heart model for use with the human fetus model of the apparatus of FIG. 1.

FIG. 6 depicts a block diagram of heart model 54 coupled to pump unit 58. In the embodiment shown, pump unit 58 comprises a power source 102 coupled to a variable timing circuit 106 and a pump motor 110. Power source 102 can comprise, for example, one or more batteries and/or an alternating current (AC) adapter for use with a standard 110V wall plug. Timing circuit 106 can comprise any suitable controller or timer for periodically activating pump motor 110 to pump fluid to heart model 54 through tube 62 to simulate a fetal heartbeat. In the embodiment shown, timing circuit 106 is variable to simulate various heart rates, and comprises a knob or other structure (e.g., button(s)) 112 to permit a user to adjust the heart rate of a simulated fetal heartbeat. In some embodiments, heart model 54 includes a length of flexible tubing 114 or other conduit extending between the body of heart model 54 and connector 74, and includes a length of flexible tubing 118 or other conduit extending between the body of heart model 54 and connector 78. In such embodiments, and as indicated in FIG. 6, tubes 114 and 118 can extend out of a (e.g., silicone or plastic) bag 122 that defines compartment 26 such that fetus models can be interchanged into and out of housing 14 without having to remove or reintroduce fluid in compartment 26.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. An apparatus comprising:
   a container having an anterior wall, a posterior wall, and an internal compartment;
   a human fetus model disposed in the compartment; and
   a liquid disposed in the compartment;
   where the anterior wall is configured to permit sonogram imaging of the human fetus model through the anterior wall; and
   where the container is configured to be removably coupled to the abdomen of a live human or human model such that the compartment simulates the uterus of the human or model.

2. The apparatus of claim 1, further comprising:
   a placenta model disposed in the compartment.

3. The apparatus of claim 2, further comprising:
   an umbilical cord model coupled to and extending between the human fetus model and the placenta model.

4. An apparatus comprising:
   a container having an anterior wall, a posterior wall, and an internal compartment configured to receive a human fetus model and a liquid;
   where the anterior wall is configured to permit sonogram imaging of the compartment through the anterior wall; and
   where the container is configured to be removably coupled to the abdomen of a live human or human model such that the compartment simulates the uterus of the human or model.

5. The apparatus of claim 4, further comprising a human fetus model configured to be disposed in the compartment of the container such that the human fetus model can be imaged through the anterior wall by sonogram.

6. The apparatus of claim 5, further comprising a liquid configured to be disposed in the compartment of the container with the human fetus model such that the fetus can be imaged through the anterior wall by sonogram.

7. The apparatus of claim 4, further comprising:
   a placenta model configured to be disposed in the compartment of the container such that the placenta model can be imaged through the anterior wall by sonogram.

8. The apparatus of claim 7, further comprising:
   an umbilical cord model coupled to and extending between the human fetus model and the placenta model.

9. The apparatus of claim 1, where the container comprises an access point through which liquid can be removed from or introduced into the compartment.

10. The apparatus of claim 9, where the access point is configured such that a human fetus model can be removed from or introduced into the compartment.

11. The apparatus of claim 5, where the human fetus model comprises a hydraulic heart model, and the apparatus further comprises:
    a pump configured to be coupled to the heart model to simulate a heartbeat by pumping liquid to the heart model.

12. The apparatus of claim 5, where the human fetus model comprises:
    a skull model; and
    a brain model disposed in the skull, the brain model configured to be distinguishable from the skull model in a sonogram image.

13. The apparatus of claim 5, where the human fetus model comprises:
    one or more bone models disposed in the human fetus model, the one or more bone models configured to be distinguishable from other parts of the human fetus model in a sonogram image.

14. The apparatus of claim 4, where the anterior wall has a flexible outer surface.

15. The apparatus of claim 14, where the anterior wall comprises silicone.

16. The apparatus of claim 15, where the posterior wall comprises silicone.

17. The apparatus of claim 14, where the anterior wall is configured to be punctured by a needle, and to substantially self-seal the puncture after removal of the needle.

18. The apparatus of claim 17, where the posterior wall is configured to resist being punctured by a needle.

19. The apparatus of claim 4, where the anterior wall is unitary with the posterior wall.

20. A kit comprising:
    an apparatus of claim 5; and
    a second human fetus model.

21. The kit of claim 20, where the second human fetus model is configured to represent a different stage of fetal development than the first human fetus model.

22. A method comprising:
generating one or more images of the compartment of an apparatus using a sonogram machine;
where the apparatus comprises:
- a container having an anterior wall, a posterior wall, and an internal compartment;
- a human fetus model disposed in the compartment; and
- a liquid disposed in the compartment;
- where the anterior wall is configured to permit sonogram imaging of the human fetus model through the anterior wall; and
- where the container is configured to be removably coupled to the abdomen of a live human or human model such that the compartment simulates the uterus of the human or model.

23. The method of claim 22, further comprising:
disposing the apparatus on the abdomen of a live human or human model such that the compartment simulates the uterus of the human or model.

* * * * *